(12) United States Patent
Raisanen

(10) Patent No.: US 6,726,882 B2
(45) Date of Patent: Apr. 27, 2004

(54) HYDROCARBON DETECTOR DEVICE

(76) Inventor: Walfred R. Raisanen, 15850 E. Graystone, Fountain Hills, AZ (US) 85268

( * ) Notice: Subject to any disclaimer, the term of this patent is extended or adjusted under 35 U.S.C. 154(b) by 291 days.

(21) Appl. No.: 09/897,857

(22) Filed: Jul. 2, 2001

(65) Prior Publication Data

US 2003/0003019 A1 Jan. 2, 2003

(51) Int. Cl.[7] ............... G01N 27/00; G01N 21/00; G01N 9/00; G01N 30/02; G01D 18/00
(52) U.S. Cl. ............... 422/98; 422/50; 422/83; 422/88; 422/90; 422/93; 422/94; 422/95; 436/139; 436/143; 436/144; 73/1.01; 73/1.02; 73/23.2; 73/23.35; 73/23.38
(58) Field of Search ............... 422/50, 83, 88, 422/90, 93, 94, 95, 98; 436/139, 143, 144; 73/1.01, 1.02, 23.2, 23.35, 23.38

(56) References Cited

U.S. PATENT DOCUMENTS

| | | | |
|---|---|---|---|
| 4,019,863 A | * 4/1977 | Jenkins et al. | 250/304 |
| 4,058,802 A | * 11/1977 | Meyers | 340/517 |
| 4,250,142 A | 2/1981 | Kollmai | 422/68 |
| 5,521,381 A | 5/1996 | Gregg et al. | 250/288 |
| 6,094,968 A | * 8/2000 | Scheufler et al. | 73/23.2 |
| 6,155,160 A | * 12/2000 | Hochbrueckner | 99/331 |

* cited by examiner

*Primary Examiner*—Jill Warden
*Assistant Examiner*—Brian Sines
(74) *Attorney, Agent, or Firm*—Jordan M. Meschkow; Lowell W. Gresham; Meschkow & Gresham, PLC

(57) ABSTRACT

A hydrocarbon detector (20) includes a gas stream delivery element (26) configured to discharge a carrier gas (70) onto a surface (24). The carrier gas (70) serves to volatilize a hydrocarbon presence (22) from the surface (24). A gas stream recovery element (28) is configured to aspirate a sample gas (78) formed from the carrier gas (70) combined with the hydrocarbon presence (22) volatilized from the surface (24). A hydrocarbon sensor (58) detects the hydrocarbon presence (22) in the sample gas (78) and generates an output signal indicative of the hydrocarbon presence (22). An indicator (80) receives the output signal and indicates the hydrocarbon presence (22) in the sample gas (78). A heat source (72) coupled to the gas stream delivery element (26) heats the carrier gas (70) to further aid in the volatilization of the hydrocarbon presence (22).

15 Claims, 2 Drawing Sheets

HYDROCARBON DETECTOR DEVICE

TECHNICAL FIELD OF THE INVENTION

The present invention relates to the field of contamination detection devices. More specifically, the present invention relates to a detector that detects residual hydrocarbon contamination on a surface.

BACKGROUND OF THE INVENTION

Parts and equipment cleaning is an integral part of a wide range of major industries such as aerospace, electronics equipment and computer manufacture, medical equipment manufacture, chemical manufacturing, and so forth. Indeed many applications of machined parts require the utmost cleanliness in the part exterior surfaces for successful application in their intended use. In all of these industry segments, large quantities of hazardous solvents are routinely employed, and eventually find their way into a waste stream, or are emitted into the air. Two major solvent waste generating mechanisms include unnecessary overcleaning and undercleaning.

In order to minimize cleaning problems, some industries use procedures that overclean most parts in the hopes of adequately cleaning all of the parts. Unfortunately, large volumes of hazardous and volatile solvents are often wasted when overcleaning parts. Solvents are also wasted through the use of improper undercleaning procedures. That is, industrial parts that were improperly cleaned the first time, i.e., undercleaned, must be recleaned, which further generates solvent waste. The solvents wasted through the practices of overcleaning and recleaning parts exacerbate the problem of water and air pollution by cleaning solvents. To avoid such waste, industry leaders are continually seeking to use cleaning solvents in as efficient and conservative a manner as possible by improving cleaning solvents and parts cleaning procedures.

Hydrocarbon-based cleaning solvents are often used to clean the exterior surfaces of machined parts following manufacture. Improper cleaning procedures, both overcleaning and rework due to undercleaning, can result in a residual layer of hydrocarbon contamination from the cleaning solvent itself on the surface of the machined part. Residual hydrocarbon contamination can cause quality and reliability problems with the machined parts, resulting in costly, and sometimes dangerous, parts failure.

Verification techniques for detecting hydrocarbon contamination and other contaminants on machined parts are sometimes used to ensure the efficacy of cleaning procedures. Unfortunately, the verification techniques involve lengthy and error prone analytical laboratory procedures. Due to the expense and delay of such laboratory analyses, they are typically only used as spot checks of cleaning performance. This leaves open the possibility for contaminated parts escaping the quality control process, leading to expensive field failures. Moreover, since such tests have turnaround times of several days or longer, the laboratory analyses may not identify a problem until many parts have been improperly cleaned.

SUMMARY OF THE INVENTION

Accordingly, it is an advantage of the present invention that a hydrocarbon detector is provided.

It is another advantage of the present invention is that a hydrocarbon detector is provided that conveniently and cost effectively screens machined parts for hydrocarbon contamination.

It is another advantage of the present invention that a hydrocarbon detector is provided that can present real-time cleaning verification feedback in an industrial production line environment.

Yet another advantage of the present invention that a hydrocarbon detector is provided that is a handheld, self-contained unit.

The above and other advantages of the present invention are carried out in one form by a portable hydrocarbon detector for detecting a hydrocarbon presence on a surface. The detector includes a gas stream delivery element having a delivery element outlet configured to discharge a carrier gas onto the surface, the carrier gas serving to volatilize the hydrocarbon presence from the surface. The detector further includes a gas stream recovery element having a recovery element inlet configured to aspirate a sample gas formed from the carrier gas combined with the hydrocarbon presence volatilized from the surface. A hydrocarbon sensor, in fluid communication with the gas stream recovery element, detects the hydrocarbon presence in the sample gas and generates an output signal indicative of the hydrocarbon presence. An indicator is coupled to the hydrocarbon sensor for receiving the output signal and indicating the hydrocarbon presence in the sample gas.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
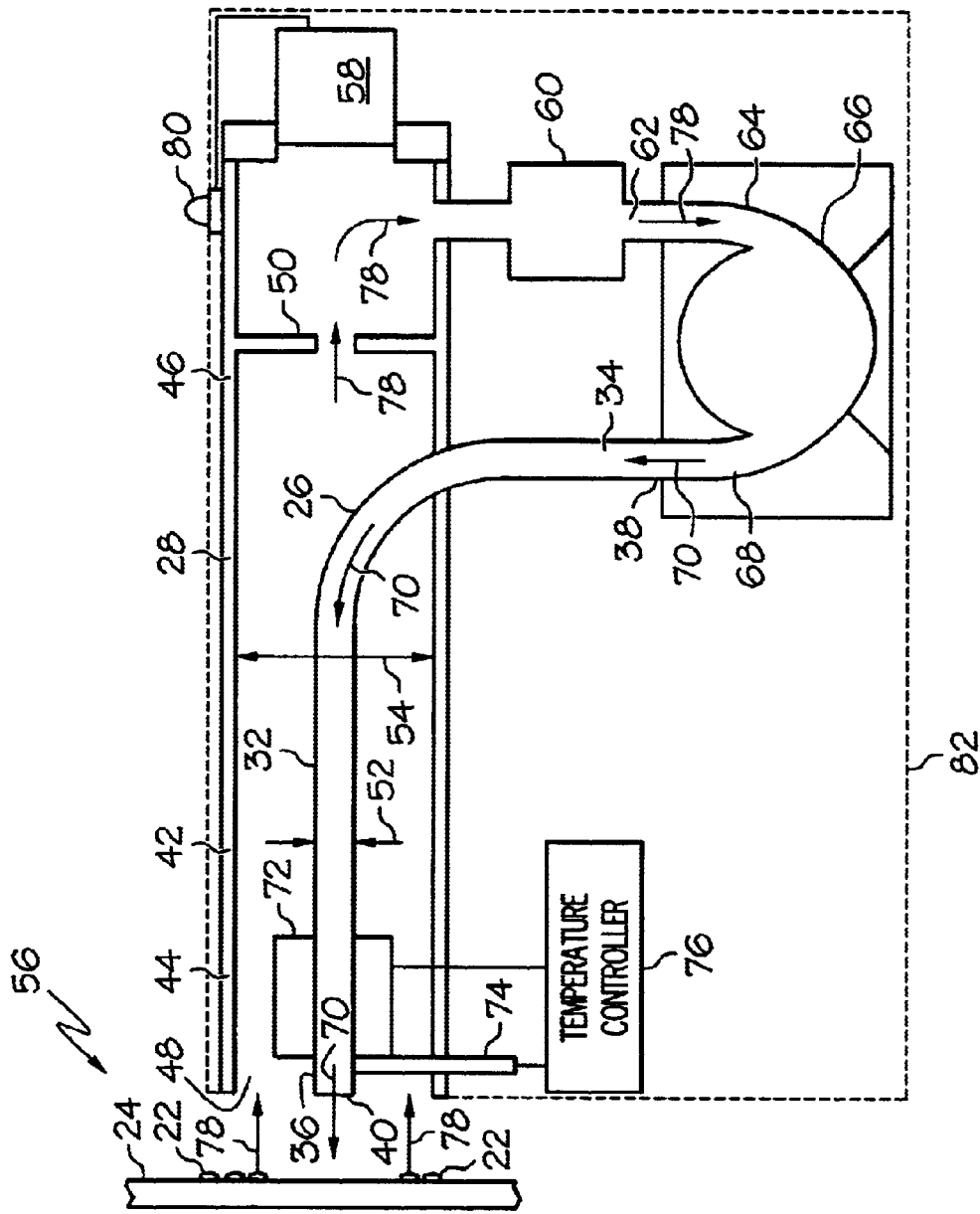
FIG. 1 shows a block diagram of a hydrocarbon detector in accordance with a preferred embodiment of the present invention.

FIG. 1 shows a block diagram of a hydrocarbon detector 20 in accordance with a preferred embodiment of the present invention. Hydrocarbon detector 20 is configured to detect a hydrocarbon presence 22 on a surface 24 of a machined part. In a preferred embodiment, hydrocarbon detector 20 is a hand-held device that may be readily utilized by a technician to screen some or all of a plurality of machined parts for the presence of residual hydrocarbon contamination remaining on surface 24 following a cleaning procedure that employs a hydrocarbon-based cleaning solvent. Thus, detector 20 provides rapid, qualitative verification of the efficacy of the cleaning procedure.

Hydrocarbon detector 20 includes a gas stream delivery element 26 and a gas stream recovery element 28. Gas stream delivery element 26 includes a first tube segment 32 having an inlet end 34 and an outlet end 36. A delivery element inlet 38 is located at inlet end 34 and a delivery element outlet 40 is located at outlet end 36. Gas stream recovery element 28 includes a second tube segment 42 having an inlet end 44 and an outlet end 46. A recovery element inlet 48 is located at inlet end 44 and a recovery element outlet 50 is located at outlet end 46.

Gas stream delivery element 26 and gas stream recovery element 28 are formed from a substantially hydrocarbon free material. A preferred hydrocarbon free material is copper tubing because it is inexpensive and malleable. However, other metals may be used. Alternatively, plastics that do not release hydrocarbons, such as polycarbonate, may be used to form gas stream delivery element 26 and gas stream recovery element 28.

In an exemplary embodiment, first tube segment 32 is located inside of and axially aligned with second tube segment 42. In other words, first tube segment 32 has an outer diameter 52 that is smaller than an inner diameter 54 of second tube segment 42. In addition, outlet end 36 of first tube segment 32, having delivery element outlet 40, is located at a gas stream transfer side 56 of detector 20. Likewise, inlet end 44 of second tube segment 42, having recovery element inlet 48, is located at gas stream transfer side 56 of detector 20.

A hydrocarbon sensor 58 is in fluid communication with outlet end 46 of gas stream recovery element 28. Hydrocarbon sensor 58 is configured to detect microgram levels of volatilized hydrocarbons. Hydrocarbon sensor 58 may be a solid state gas sensing device, a photo-ionization sensor, and the like that is capable of real-time detection of small quantities of contaminants to a high degree of precision, while at the same time being inexpensive and reliable.

A filter 60 is positioned downstream from hydrocarbon sensor 58. In an exemplary embodiment, filter 60 is an activated charcoal filter. However, zeolite (microporous silicate or aluminosilicate structured minerals) or other materials may also be employed as filter 60.

An outlet 62 of filter 60 is in fluid communication with an inlet port 64 of a recirculation pump 66, while an outlet port 68 of recirculation pump 66 is in fluid communication with inlet end 34 of gas stream delivery element 26.

In operation, gas stream transfer side 56 of hydrocarbon detector 20 is held proximate surface 24. When detector 20 is activated, recirculation pump 66 begins circulating a carrier gas, represented by arrows 70 through detector 20. More particularly, carrier gas 70 is pumped from outlet port 68 of recirculation pump 66. Carrier gas 70 is subsequently pushed through first tube segment 32 of gas stream delivery element 26 and discharged from delivery element outlet 40 onto surface 24. Carrier gas 70 serves to volatilize, or evaporate, hydrocarbon presence 22 from surface 24.

To augment this volatilization, a heat source 72 is coupled to gas stream delivery element 26. In a preferred embodiment, heat source 72 is an electrical resistance device that wraps around and heats first tube segment 32. Heat from first tube segment 32 subsequently heats carrier gas 70 traveling through gas stream delivery element 26. Those skilled in the art will recognize that other heaters may be used, such as a Nichrome wire or coil, an infrared heater, a quartz heater, and the like for heating carrier gas 70.

A temperature sensor 74 is in communication with gas stream delivery element 26 at outlet end 36. Temperature sensor 74 may be a bead thermistor, a thermocouple, and the like for detecting a temperature of carrier gas 70 discharged from delivery element outlet 40. A temperature controller 76 is electrically connected to temperature sensor 74 and heat source 72. Temperature controller 76 receives the temperature signal and controls heat source 72 in response to the received temperature signal. Temperature controller 76 varies the average electrical power applied to heat source 72 to maintain a constant temperature in heat source 72. Temperature controller 76 may also include an external control (not shown) that may be adjusted to decrease or increase the heat produced by heat source 72.

Heated carrier gas 70 is discharged from delivery element outlet 40 onto surface 24. The flow rate of carrier gas 70 onto surface 24 combined with the heat of carrier gas 70 effectively volatilizes hydrocarbon presence 22 from surface 24. A sample gas, represented by an arrow 78, is aspirated, or drawn, into recovery element inlet 48 of gas stream recovery element 28 through suction caused by recirculation pump 66. Sample gas 78 is formed from a combination of carrier gas 70 and hydrocarbon presence 22 volatilized from surface 24.

A first flow rate of carrier gas 70 from delivery element outlet 40 is greater than a second flow rate of sample gas 78 into recovery element inlet 48. The differing flow rates occur due to a difference in cross-sectional area between first tube segment 32 and second tube segment 42. For example, first tube segment 32 may have an inner diameter that is one quarter the size of the inner diameter of second tube segment 42. A greater flow rate of carrier gas 70 from delivery element outlet 40 than the flow rate of sample gas 78 into recovery element inlet 48 is desirable so that carrier gas 70 will thoroughly impinge surface 24 prior to being drawn into recovery element inlet 48 as sample gas 78.

In addition, the tube within a tube arrangement of first and second tube segments 32 and 42, respectively, effectively captures hydrocarbon presence 22 volatilized from surface 24 for subsequent detection at hydrocarbon sensor 58. Although first tube segment 32 of gas stream delivery element 26 is positioned within second tube segment 42 of gas stream recovery element 28, it should be understood that the opposite configuration will also result in the effective capture of hydrocarbon presence 22. That is, a tube segment of a gas stream delivery element may be larger than a tube segment of a gas stream recovery element so that the gas stream recovery element tube segment may be located inside of and axially aligned with the gas stream delivery element tube segment.

Sample gas 78 is drawn through second tube segment 42 and exits recovery element outlet 50 where hydrocarbon sensor 58 detects hydrocarbon presence 22 in sample gas 78. Hydrocarbon sensor 58 generates an output signal indicative of hydrocarbon presence 22. For example, hydrocarbon sensor 58 may generate a simple analog signal indicating a detectable presence of hydrocarbon in sample gas 78.

An indicator 80 is electrically coupled to hydrocarbon sensor 58. Indicator 80 receives the output signal from hydrocarbon sensor 58. In an exemplary embodiment, indicator 80 is a light emitting diode (LED) that illuminates when the output signal exceeds a particular threshold. For example, indicator 80 may be a two-color LED. Thus, indicator 80 illuminates in a first color, i.e., green, when the output signal from hydrocarbon sensor 58 is below the illumination threshold. Accordingly, indicator 80 is illuminated green, in response to an absence of detectable hydrocarbon presence 22 in sample gas 78. Similarly, when the output signal from hydrocarbon sensor 58 is above the illumination threshold, indicator 80 illuminates in a second color, i.e., red, indicating hydrocarbon presence 22 in sample gas 78. When hydrocarbon presence 22 is substantially completely volatilized from surface 24 and is no longer detectable by hydrocarbon sensor 58 in sample gas 78, indicator 80 illuminates in the first color, i.e., green, indicating the absence of hydrocarbon presence 22.

In an alternative embodiment, indicator 80 may be a single-color LED, and detector 20 may include a second single-color LED. As such, detector 20 may be configured such that one of the LEDs illuminates in one color (i.e., red) when hydrocarbon presence 22 is detected in sample gas 78, and the other LED illuminates in a different color (i.e., green) in the absence of hydrocarbon presence 22. Although indicator 80 is described in terms of a light emitting diodes, it should be understood that other indicators, such as audible tones, LCD displays, analog meters, and so forth may be used.

Sample gas 78 is subsequently filtered downstream from hydrocarbon sensor 58 by filter 60 to remove hydrocarbon presence 22 and other contaminants from sample gas 78. Sample gas 78 from filter 60 is then returned to gas stream delivery element 26 as carrier gas 70 absent hydrocarbon presence 22.

All of the components of hydrocarbon detector 20, discussed above, including a battery power source are packaged in a common hand-held housing, represented by dashed lines 82. Housing 82 is desirably shaped for ready grip by the user. For example, housing 82 may be barrel-shaped, like that of a flashlight. Alternatively, housing 82 may include a hand grip, like that of a handgun. Detector 20 may include a pushbutton or trigger switch for activating detector 20.

The portable structure of hydrocarbon detector 20, battery operation, and indicator 80 allows a technician to obtain a qualitative indication of hydrocarbon presence 22 on some or all of a plurality of machined parts and equipment. Hydrocarbon detector 20 can be used to present real-time cleaning verification feedback in an industrial production line environment or in the field. This cleaning verification feedback can be used to optimize the quantity of cleaning solvent that is used in an equipment cleaning process so that waste of the solvent due to overcleaning and recleaning due to undercleaning is minimized.

Figure 2:
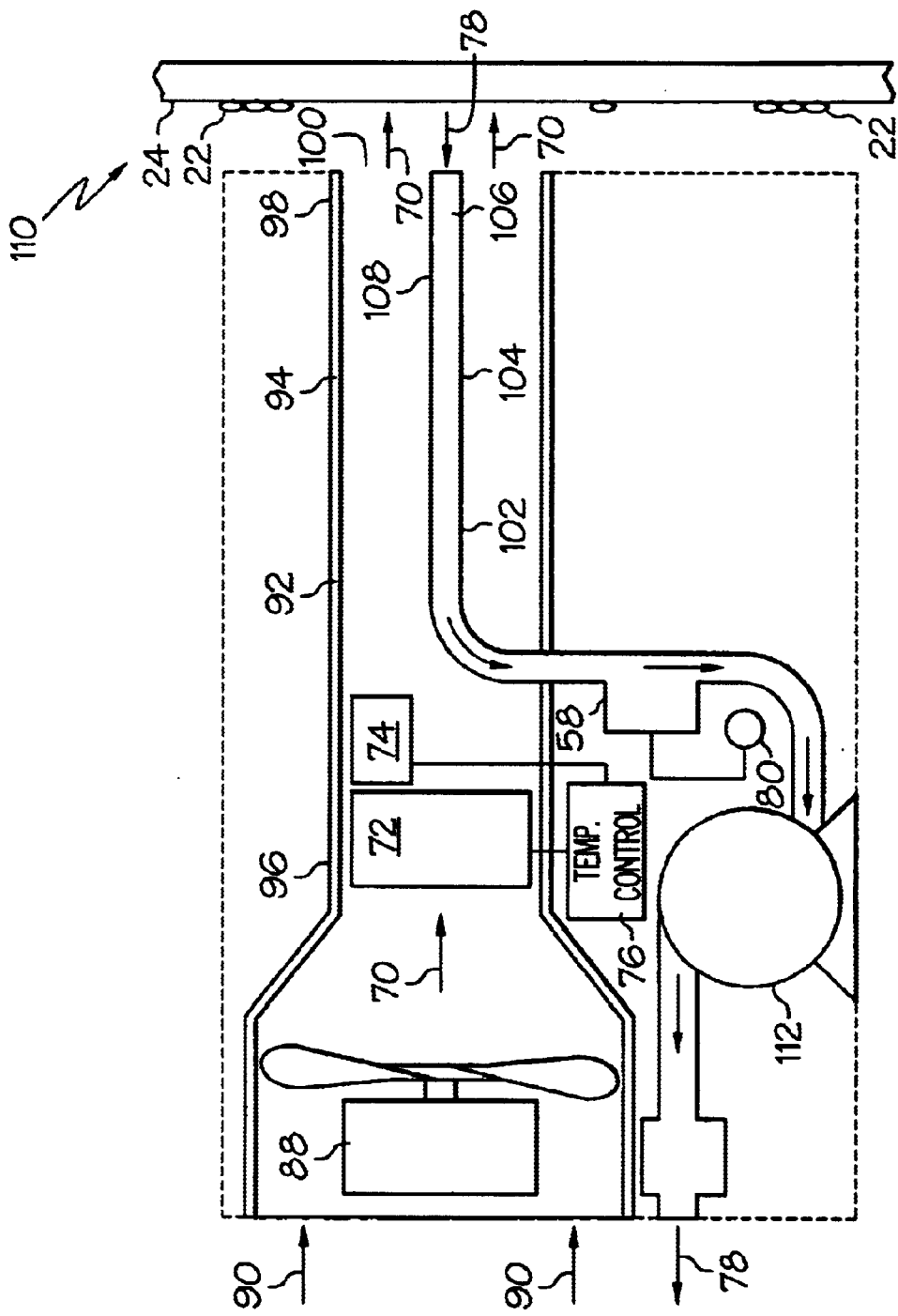
FIG. 2 shows a block diagram of a hydrocarbon detector in accordance with an alternative embodiment of the present invention.

FIG. 2 shows a block diagram of a hydrocarbon detector 86 in accordance with an alternative embodiment of the present invention. Hydrocarbon detector 86 is a dual pump system (discussed below) that permits a user to change the flow rate of sample gas 78 independent from carrier gas 70. This variable flow rate feature allows a user to adjust detector 86 to a flow rate specific to a particular hydrocarbon sensor being used.

Hydrocarbon detector 86 includes a carrier gas source, or fan, 88 for drawing external air 90 into detector 86 to serve as carrier gas 70. Detector 86 further includes a gas stream delivery element 92 having a first tube segment 94 that has a delivery element inlet end 96 coupled to an outlet of carrier gas source 88 for receiving carrier gas 70. Heat source 72 is coupled to gas stream delivery element 92 for heating carrier gas 70 to aid in the volatilization of hydrocarbon presence 22. Detector 86 further includes temperature sensor 74 for detecting a temperature of carrier gas 70 and temperature controller 76 interposed between temperature sensor 74 and heat source 72 for maintaining temperature control of heat source 72, as discussed above. A delivery element outlet end 98 of first tube segment 94 includes a delivery element outlet 100 configured to discharge heated carrier gas 70 onto surface 24.

A gas stream recovery element 102 includes a second tube segment 104 and a recovery element inlet 106 located at a recovery element inlet end 108 of second tube segment 104. Recovery element inlet 106 is configured to aspirate sample gas 78, including hydrocarbon presence 22 volatilized from surface 24. Second tube segment 104 is located inside of, and axially aligned with, first tube segment 94. In addition, delivery element outlet end 98 and recovery element inlet end 108 are positioned at a gas stream transfer side 110 of detector 86.

A carrier gas sample pump 112 is in fluid communication with gas stream recovery element 102. Carrier gas sample pump 112 pulls sample gas 78 through gas stream recovery element 102 and past hydrocarbon sensor 58 interposed between gas stream recovery element 102 and pump 112. As discussed above, hydrocarbon sensor 58 detects hydrocarbon presence 22 in sample gas 78 and generates an output signal indicative of hydrocarbon presence 22. Indicator 80, electrically coupled to hydrocarbon sensor, receives the output signal and subsequently indicates the presence or absence of hydrocarbons in sample gas 78, as discussed above.

Carrier gas sample pump 112 further pushes sample gas 78 through filter 60 located downstream from hydrocarbon sensor 50 prior to releasing sample gas 78, absent hydrocarbon presence 22, from detector 86.

In summary, the present invention teaches of a hydrocarbon detector that is a handheld, self-contained unit. The hydrocarbon detector presents real-time qualitative detection of hydrocarbon contamination on machined parts and equipment. Through the use of the hydrocarbon detector, cleaning verification feedback can be conveniently and cost effectively obtained in an industrial production line environment as well as in the field.

Although the preferred embodiments of the invention have been illustrated and described in detail, it will be readily apparent to those skilled in the art that various modifications may be made therein without departing from the spirit of the invention or from the scope of the appended claims. For example, the present invention is not limited to the detection of hydrocarbon contamination. For example, the hydrocarbon sensor may be replaced by another sensor that can detect different volatile contaminants, such as heavy grease, silicone oils, and so forth. In addition, the heat produced by heat source can be adjusted to more effectively volatilize these other volatile contaminants.

What is claimed is:

1. A hydrocarbon detector for detecting a hydrocarbon presence on a surface, said detector comprising:
    a gas stream delivery element having a delivery element outlet configured to discharge a carrier gas onto said surface, said carrier gas serving to volatilize said hydrocarbon presence from said surface, said gas stream delivery element including a first tube segment, and said delivery element outlet being located at an outlet end of said first tube segment;
    a gas stream recovery element having a recovery element inlet configured to aspirate a sample gas formed from said carrier gas combined with said hydrocarbon presence volatilized from said surface, said gas stream recovery element including a second tube segment, said recovery element inlet being located at an inlet end of said second tube segment, said first tube segment being located inside of and axially aligned with said second tube segment, and said first and second ends being positioned at a gas stream transfer side of said detector;
    a hydrocarbon sensor, in fluid communication with said gas stream recovery element, for detecting said hydrocarbon presence in said sample gas and generating an output signal indicative of said hydrocarbon presence; and
    an indicator coupled to said hydrocarbon sensor for receiving said output signal and indicating said hydrocarbon presence in said sample gas.

2. A hydrocarbon detector for detecting a hydrocarbon presence on a surface, said detector comprising:
    a gas stream delivery element having a delivery element outlet configured to discharge a carrier gas onto said surface, said carrier gas serving to volatilize said hydrocarbon presence from said surface, said gas stream delivery element inlet including a first tube segment, said delivery element outlet being located at an outlet end of said first tube segment;

a gas stream recovery element having a recovery element inlet configured to aspirate a sample gas formed from said carrier gas combined with said hydrocarbon presence volatilized from said surface, said gas stream recovery element including a second tube segment, said recovery element inlet being located at an inlet end of said second tube segment, said second tube segment being located inside of and axially aligned with said first tube segment, and said first and second ends being positioned at a gas stream transfer side of said detector;

a hydrocarbon sensor, in fluid communication with said gas stream recovery element, for detecting said hydrocarbon presence in said sample gas and generating an output signal indicative of said hydrocarbon presence; and an indicator coupled to said hydrocarbon sensor for receiving said output signal and indicating said hydrocarbon presence in said sample gas.

3. A hydrocarbon detector for detecting a hydrocarbon presence on a surface, said detector comprising:

a gas stream delivery element having a delivery element outlet configured to discharge a carrier gas onto said surface, said carrier gas serving to volatilize said hydrocarbon presence from said surface;

a gas stream recovery element having a recovery element inlet configured to aspirate a sample gas formed from said carrier gas combined with said hydrocarbon presence volatilized from said surface, said gas stream delivery and said gas stream recovery elements being formed from a substantially hydrocarbon free material;

a hydrocarbon sensor, in fluid communication with said gas stream recovery element, for detecting said hydrocarbon presence in said sample gas and generating an output signal indicative of said hydrocarbon presence; and an indicator coupled to said hydrocarbon sensor for receiving said output signal and indicating said hydrocarbon presence in said sample gas.

4. A hydrocarbon detector for detecting a hydrocarbon presence on a surface, said detector comprising:

a gas stream delivery element having a delivery element outlet configured to discharge a carrier gas onto said surface, said carrier gas serving to volatilize said hydrocarbon presence from said surface;

a heat source coupled to said gas stream delivery element for heating said carrier gas to aid in the volatilization of said hydrocarbon presence;

a temperature sensor in communication with said gas stream delivery element for detecting a temperature of said carrier gas discharged from said delivery element outlet and generating a temperature signal in response to said temperature;

a temperature controller for receiving said temperature signal and controlling said heat source in response to said temperature signal;

a gas stream recovery element having a recovery element inlet configured to aspirate a sample gas formed from said carrier gas combined with said hydrocarbon presence volatilized from said surface;

a hydrocarbon sensor, in fluid communication with said gas stream recovery element, for detecting said hydrocarbon presence in said sample gas and generating an output signal indicative of said hydrocarbon presence; and an indicator coupled to said hydrocarbon sensor for receiving said output signal and indicating said hydrocarbon presence in said sample gas.

5. A hydrocarbon detector for detecting a hydrocarbon presence on a surface, said detector comprising:

a gas stream delivery element having a delivery element outlet configured to discharge a carrier gas onto said surface, said carrier gas serving to volatilize said hydrocarbon presence from said surface;

a gas stream recovery element having a recovery element inlet configured to aspirate a sample gas formed from said carrier gas combined with said hydrocarbon presence volatilized from said surface;

a hydrocarbon sensor, in fluid communication with said gas stream recovery element, for detecting said hydrocarbon presence in said sample gas and generating an output signal indicative of said hydrocarbon presence;

a filter positioned downstream from said hydrocarbon sensor, said filter removing said hydrocarbon presence from said sample gas; and an indicator coupled to said hydrocarbon sensor for receiving said output signal and indicating said hydrocarbon presence in said sample gas.

6. A hydrocarbon detector as claimed in claim 5 further comprising a recirculation pump having an inlet port and an outlet port, said inlet port being in fluid communication with an outlet of said filter and said outlet port being in fluid communication with a delivery element inlet of said gas stream delivery element, said recirculation pump returning said sample gas from said filter to said gas stream delivery element as said carrier gas absent said hydrocarbon presence.

7. A hydrocarbon detector for detecting a hydrocarbon presence on a surface, said detector comprising:

a gas stream delivery element having a delivery element outlet configured to discharge a carrier gas onto said surface, said carrier gas serving to volatilize said hydrocarbon presence from said surface, and said carrier gas being external air;

a carrier gas source in fluid communication with said gas stream delivery element, said carrier gas source drawing said external air into said gas stream delivery element;

a gas stream recovery element having a recovery element inlet configured to aspirate a sample gas formed from said carrier gas combined with said hydrocarbon presence volatilized from said surface;

a hydrocarbon sensor, in fluid communication with said gas stream recovery element, for detecting said hydrocarbon presence in said sample gas and generating an output signal indicative of said hydrocarbon presence;

an indicator coupled to said hydrocarbon sensor for receiving said output signal and indicating said hydrocarbon presence in said sample gas; and a carrier gas sample pump in fluid communication with said gas stream recovery element, said carrier gas sample pump pulling said sample gas from said gas stream recovery element and releasing said sample gas from said hydrocarbon detector.

8. A hydrocarbon detector for detecting a hydrocarbon presence on a surface, said detector comprising:

a gas stream delivery element having a delivery element outlet configured to discharge a carrier gas onto said surface, said carrier gas serving to volatilize said hydrocarbon presence from said surface;

a gas stream recovery element having a recovery element inlet configured to aspirate a sample gas formed from said carrier gas combined with said hydrocarbon presence volatilized from said surface;

a hydrocarbon sensor, in fluid communication with said gas stream recovery element, for detecting said hydrocarbon presence in said sample gas and generating an output signal indicative of said hydrocarbon presence; and a light emitting diode (LED) coupled to said hydrocarbon sensor for receiving said output signal and indicating said hydrocarbon presence in said sample gas, said LED being a two-color LED, said LED illuminating in a first color in response to said hydrocarbon presence in said sample gas, and said LED illuminating in a second color in response to an absence of said hydrocarbon presence in said sample gas.

9. A hydrocarbon detector for detecting a hydrocarbon presence on a surface, said detector comprising:

a gas stream delivery element having a delivery element outlet configured to discharge a carrier gas onto said surface, said carrier gas serving to volatilize said hydrocarbon presence from said surface;

a gas stream recovery element having a recovery element inlet configured to aspirate a sample gas formed from said carrier gas combined with said hydrocarbon presence volatilized from said surface;

a hydrocarbon sensor, in fluid communication with said gas stream recovery element, for detecting said hydrocarbon presence in said sample gas and generating an output signal indicative of said hydrocarbon presence;

a first light emitting diode (LED) coupled to said hydrocarbon sensor for receiving said output signal and indicating said hydrocarbon presence in said sample gas, said LED illuminating in response to said hydrocarbon presence in said sample gas; and a second LED, said second LED illuminating in response to an absence of said hydrocarbon presence in said sample gas.

10. A hydrocarbon detector for detecting a hydrocarbon presence on a surface, said detector comprising:

a carrier gas source for drawing external air into said detector to serve as a carrier gas;

a gas stream delivery element including a first tube segment, said first tube segment having an inlet end coupled to said carrier gas source for receiving said carrier gas and having an outlet end, said outlet end having a delivery element outlet configured to discharge said carrier gas onto said surface, said carrier gas serving to volatilize said hydrocarbon presence from said surface;

a gas stream recovery element including a second tube segment and a recovery element inlet located at a recovery inlet end of said second tube segment, said second tube segment being located inside of and axially aligned with said first tube segment, said outlet end and said recovery inlet end being positioned at a gas stream transfer side of said detector, and said recovery element inlet being configured to aspirate a sample gas formed from said carrier gas combined with said hydrocarbon presence volatilized from said surface;

a carrier gas sample pump in fluid communication with said gas stream recovery element, said carrier gas sample pump pulling said sample gas through said gas stream recovery element and releasing said sample gas from said hydrocarbon detector;

a hydrocarbon sensor interposed between said gas stream recovery element and said carrier gas sample pump, said hydrocarbon sensor detecting said hydrocarbon presence in said sample gas and generating an output signal indicative of said hydrocarbon presence; and an indicator coupled to said hydrocarbon sensor for receiving said output signal and indicating said hydrocarbon presence in said sample gas.

11. A hydrocarbon detector as claimed in claim 10 further comprising a heat source coupled to said gas stream delivery element for heating said carrier gas to aid in the volatilization of said hydrocarbon presence.

12. A hydrocarbon detector as claimed in claim 10 further comprising a filter positioned downstream from said hydrocarbon sensor, said filter removing said hydrocarbon presence from said sample gas.

13. A hydrocarbon detector for detecting a hydrocarbon presence on a surface, said detector comprising:

a gas stream delivery element having a delivery element outlet configured to discharge a carrier gas onto said surface, said carrier gas serving to volatilize said hydrocarbon presence from said surface;

a heat source coupled to said gas stream delivery element for heating said carrier gas to aid in the volatilization of said hydrocarbon presence;

a gas stream recovery element having a recovery element inlet configured to aspirate a sample gas formed from said carrier gas combined with said hydrocarbon presence volatilized from said surface;

a hydrocarbon sensor in fluid communication with said gas stream recovery element, said hydrocarbon sensor detecting said hydrocarbon presence in said sample gas and generating an output signal indicative of said hydrocarbon presence;

a filter positioned downstream from said hydrocarbon sensor, said filter removing said hydrocarbon presence from said sample gas; and an indicator coupled to said hydrocarbon sensor for receiving said output signal and indicating said hydrocarbon presence in said sample gas.

14. A hydrocarbon detector as claimed in claim 13 further comprising a recirculation pump having an inlet port and an outlet port, said inlet port being in fluid communication with an outlet of said filter and said outlet port being in fluid communication with a delivery element inlet of said gas stream delivery element, said recirculation pump returning said sample gas from said filter to said gas stream delivery element as said carrier gas absent said hydrocarbon presence.

15. A hydrocarbon detector as claimed in claim 13 wherein:

said gas stream delivery element includes a first tube segment, said delivery element outlet being located at a first end of said first tube segment; and said gas stream recovery element includes a second tube segment, said recovery element inlet being located at a second end of said second tube segment, said first tube segment being located inside of and axially aligned with said second tube segment, and said first and second ends being positioned at a gas stream transfer side of said detector.

* * * * *

UNITED STATES PATENT AND TRADEMARK OFFICE
CERTIFICATE OF CORRECTION

PATENT NO.  : 6,726,882 B2
DATED       : April 27, 2004
INVENTOR(S) : Walfred R. Raisanen It is certified that error appears in the above-identified patent and that said Letters Patent is hereby corrected as shown below:

<u>Column 7,</u>
Line 3, remove the word "inlet" after the word "element" and before the word "including".

Signed and Sealed this

Thirtieth Day of November, 2004

JON W. DUDAS
*Director of the United States Patent and Trademark Office*